United States Patent [19]

Horwitz et al.

[11] Patent Number: 4,574,072
[45] Date of Patent: Mar. 4, 1986

[54] METHOD FOR EXTRACTING LANTHANIDES AND ACTINIDES FROM ACID SOLUTIONS BY MODIFICATION OF PUREX SOLVENT

[75] Inventors: E. Philip Horwitz; Dale G. Kalina, both of Naperville, Ill.

[73] Assignee: The United States of America as represented by the United States Department of Energy, Washington, D.C.

[21] Appl. No.: 612,199

[22] Filed: May 21, 1984

Related U.S. Application Data

[60] Continuation-in-part of Ser. No. 608,299, May 8, 1984, which is a division of Ser. No. 517,475, Jul. 26, 1983.

[51] Int. Cl.$^3$ .............. B01D 11/04; C01F 17/00; C22B 59/00; C01G 56/00
[52] U.S. Cl. .............................. 423/9; 423/10; 423/21.5
[58] Field of Search .............. 423/8, 9, 10, 21.5; 564/15; 252/631

[56] References Cited

U.S. PATENT DOCUMENTS 3,243,254  3/1966  Siddall .................................. 423/9

OTHER PUBLICATIONS

Medved, T. Ya et al., "Dialkyl (diaryl) [dialkylcarbamoylmethyl] phosphine oxides", Lzv. Akad. Nauk. SSSR, Ser. Khim., (9), pp. 2121–2127, (1981), (Chem. Abst. 96: 35411 (1982)).

Navratil, J. D. and Martella, L. L. "Extraction Behavior of Americium and Plutonium with Mixed Solvent Extractants." Sep. Sci. and Tech., 16(9), pp. 1147–1155, 1981.

Horwitz et al., "The Extraction of Th(IV) and U(VI) by Dihexyl-N,N-diethylcarbamylmethylphosphonate from Aqueous Nitrate Media," pp. 403–416, Separation Science and Technology 16(4), (1981).

Horwitz et al., "The Extraction of Selected Transplutonium(III) and Lanthanide(III) Ions by Dihexyl-N,N-diethylcarbamoylmethylphosphonate from Aqueous Nitrate Media," Separation Science & Tech., 16(4), pp. 417–437, (1981).

Kalina et al., "The Extraction of Am(III) and Fe(III) by Selected Dihexyl-N,N-Dialkylcarbamoylmethyl-Phosphonates, -Phosphinates and -Phosphine Oxides from Nitrate Media," Separation Science & Tech., 16(9), pp. 1127–1145 (1981).

Muscatello et al., "The Extraction of Am(III) and EU-(III) From Aqueous Ammonium Thiocyanate by Dihexyl-N,N-diethylcarbamoylmethylphosphonate and Related Compounds," Separation Science & Tech., 16(6), p. 859 (1982).

(List continued on next page.)

*Primary Examiner*—Teddy S. Gron
*Assistant Examiner*—Virginia B. Caress
*Attorney, Agent, or Firm*—James W. Weinberger; Walter L. Rees; Judson R. Hightower

[57] ABSTRACT

A process for the recovery of actinide and lanthanide values from aqueous solutions with an extraction solution containing an organic extractant having the formula:

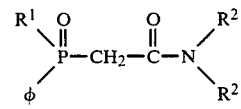

where $\phi$ is phenyl, $R^1$ is a straight or branched alkyl or alkoxyalkyl containing from 6 to 12 carbon atoms and $R^2$ is an alkyl containing from 3 to 6 carbon atoms and phase modifiers in a water-immiscible hydrocarbon diluent. The addition of the extractant to the Purex process extractant, tri-n-butylphosphate in normal paraffin hydrocarbon diluent, will permit the extraction of multivalent lanthanide and actinide values from 0.1 to 12.0 molar acid solutions.

20 Claims, 6 Drawing Figures

OTHER PUBLICATIONS

Horwitz et al., "Selected Alkyl(phenyl)-N,N-dialkyl-carbamoylmethylphosphine Oxides as Extractants for Am(III) from Nitric Acid Media," Separation Science & Tech., 17(10), pp. 1261-1279, (1982).

Horwitz et al., "Carbamoylmethylphosphoryl Derivatives as Actinide Extractants and Their Significance in the Processing and Recovery of Plutonium and other Actinides," Plutonium Chemistry, ACS Symposium Series, 216, Chapt. 22, p. 433 (1983).

Horwitz et al., "Octyl(Phenyl)-N,N-Diisobutylcarbamoylmethylphosphine Oxide as an Extractant for Actinides from Nitric Acid Waste," (ISEC '83).

Muscatello et al., "The Extraction of Americium(III) by Mixtures of Tributylphosphate with Dibutyl-N,-N-diethylcarbamoylphosphonate and -Methylphosphonate (DBDECP and DBDECMP), "Solvent Extraction & Ion Exchange, 1(1) pp. 127-139 (1983).

METHOD FOR EXTRACTING LANTHANIDES AND ACTINIDES FROM ACID SOLUTIONS BY MODIFICATION OF PUREX SOLVENT

CONTRACTUAL ORIGIN OF THE INVENTION

The U.S. Government has rights in this invention pursuant to Contract No. W-31-109-ENG-38 between the U.S. Department of Energy and Argonne National Laboratory.

This application is a continuation-in-part of Department of Energy Case No. S-61,690 entitled "Improved Method For Extracting Lanthanides And Actinides From Acid Solutions", which was deposited in the U.S. Patent Office May 8, 1984 and was assigned provisional Ser. No. 608,299, which is a divisional of application Ser. No. 517,475, filed July 26, 1983.

BACKGROUND OF THE INVENTION

This invention relates to a method for the recovery of lanthanide and actinide values from aqueous acid solutions. More specifically, the invention relates to a method for the recovery and separation of multivalent lanthanide and actinide values from aqueous acid waste solutions containing these and other values.

The disposition of the waste which results from the reprocessing of irradiated nuclear power reactor fuel elements is one of the major problems facing the nuclear power industry today. One approach is to solidify the liquid wastes as they come from the reprocessing facility into a stable solid material which can be stored in the earth for a period of time sufficient for the radiation to decay to safe levels. However, the storage times required to achieve safe levels of radioactivity are on the order of one million years. This is far longer than the geological stability of the earth can be expected to be maintained. One solution is to remove the extremely long-lived radioactive components, such as the actinides, i.e. the americium, curium, plutonium and neptunium from the waste solution so that the remaining radioactive elements, representing the bulk of the radioactive waste, need only be stored for up to 1000 years before the radioactivity decays to background levels. This time period is within the realm of determining geological integrity. The lanthanides and actinides thus recovered from the waste can then be reprocessed and recycled to provide additional fuel for nuclear reactors and for isotopic power sources.

Another approach is to minimize the volume of radioactive waste that must be buried by first removing the actinides, particularly plutonium and americium, and then removing the major heat producing isotopes $^{90}$Sr and $^{137}$Cs. The remaining waste is not sufficiently radioactive to require placement in a deep geological repository. $^{90}$Sr and $^{137}$Cs have commercial applications. Only the actinide fraction would require placement in a deep geological repository. The volume of the TRU fraction (neptunium, plutonium, and americium) together with lanthanide fission products is approximately 1% of the total high level radioactive waste generated in a plutonium production plant.

The problem with recovering the lanthanides and actinides from large volumes of acidic high-level radioactive waste solutions is to find methods, using extractants, which will do so effectively and economically, since the lanthanides and actinides are present in several valence states and are difficult to recover together.

One group of extractants which has been considered for the extraction of lanthanide and actinide values from aqueous acid waste solutions are the bidentate organophosphorous compounds. These compounds are described in U.S. Pat. No. 3,243,254 which issued Mar. 29, 1966 to Thomas Siddall III and is assigned to the common assignee. These extractants, include di-n-hexyl N,N-dibutylcarbamylmethylenephosphonate, di-n-octyl N,N-diethylcarbamylphosphonate, dibutyl N,N-diethylcarbamylphosphonate, and dihexyl N,N-diethylcarbamylmethylene phosphonate. These extractants have generally proven satisfactory, although distribution ratios for some lanthanides and actinides are small, so that separation from other values found in the reprocessing solution is not always satisfactory. Furthermore, acid concentration ranges of the feed solutions are critical to extractability and the extractants are susceptible to radiolytic and hydrolytic damage which reduce their effectiveness.

SUMMARY OF THE INVENTION

A process has been developed for the extraction of multivalent lanthanide and actinide values from acidic waste solutions, and for the separation of these values from fission product and other values, which utilizes a new series of neutral bi-functional extractants, the alkyl(phenyl)-N, N-dialkylcarbamoylmethylphosphine oxides, in combination with a phase modifier to form an extraction solution. These extraction solutions have distribution ratios for lanthanides and actinides which are significantly improved over the prior art extractants, particularly when used with normal paraffin hydrocarbon diluents (NPH). The extraction solutions are acid dependent, i.e. the extractability of the lanthanide and actinide values increases directly with increased acid concentration of the feed solution up to a range of 1 to 2 M, which simplifies recovery of the extracted values from the extractant. The extractant will recover trivalent and tetravalent lanthanide values and trivalent, tetravalent and hexavalent actinide values, so that valence adjustment in the feed solution is not necessary.

The invention is a process for the recovery of multivalent lanthanide and actinide values from an aqueous acid solution containing these and other values by adjusting the concentration of the acid solution from 0.1 to 12.0 M in acid to form a feed solution, contacting the feed solution with an extraction solution consisting of an organic extractant and a phase modifier in an inert water-immiscible diluent, the extractant having the formula:

where $\phi$ is phenyl, R' is a straight or branched alkyl or alkoxyalkyl containing from 6 to 12 carbon atoms and R" is an alkyl containing from 3 to 6 carbon atoms, the phase modifier being selected from the group of tri-n-butyl phosphate, dibutyl butylphosphonate, tris(2-ethylhexyl)-phosphine oxide dihexylsulfoxide and diethylacetamide, whereby the multivalent lanthanide and actinide values are extracted by the extraction solution, separating the extraction solution from the feed solution, and stripping the lanthanide and actinide values from the extraction solution.

Most importantly, a small amount of the organic extractant of the invention added to Purex process extractant, which is generally about 30 weight percent tri-n-butyl phosphate (TBP) in a normal paraffin hydrocarbon diluent, forms an entirely new extractant. This new extractant will recover multivalent actinide and lanthanide values from acid solutions, not otherwise readily recoverable using Purex process extractant.

It is therefore one object of the invention to provide an improved process for recovery of multivalent lanthanide and actinide values from aqueous acid solutions.

It is another object of the invention to provide an improved process for the recovery and separation of multivalent lanthanide and actinide values from fission product and other values present together in a aqueous acid nuclear waste reprocessing solutions.

It is another object of the invention to provide an improved process for recovering multivalent lanthanide and actinide values from aqueous acid solutions which utilizes an extraction solution in a normal paraffin hydrocarbon diluent.

Finally, it is the object of the invention to provide a method for modifying the Purex process extractant so that it might be used to recover multivalent actinide and lanthanide values from aqueous acid nuclear waste reprocessing solutions.

DETAILED DESCRIPTION OF THE PREFERRED EMBODIMENT

These and other objects of the invention for recovering multivalent lanthanide and actinide values from an aqueous nitric acid nuclear fuel waste reprocessing solution containing these and fission product and other values may be met by adjusting the aqueous solution to between 0.5 and 5.0 molar nitric acid and making the solution about 0.18 M in oxalic acid to form a feed solution, contacting the feed solution with an extraction solution of about 0.2 M octyl(phenyl)-N,N-diisobutyl-carbamoylmethylphosphine oxide (hereinafter referred to as O$\phi$D[IB]CMPO) and tri-n-butyl phosphate (hereinafter referred to as TBP) in normal paraffin hydrocarbon diluent, to extract the multivalent lanthanide and actinide values from the aqueous feed solution, the ratio of O$\phi$D[IB]CMPO to TBP being about 1:6, separating the loaded extraction solution from the aqueous phase, and contacting the loaded extraction solution with an aqueous solution which is about 0.01 to 0.02 M in nitric acid to strip the lanthande and actinide values from the extraction solution, thereby recovering the multivalent lanthanide and actinide values.

The process of the invention is useful for recovering lanthanide and actinide values from aqueous acid solutions containing these and fission product and metal values such as iron and zirconium. Since the extractants will remove trivalent and tetravalent lanthanides and trivalent, tetravalent and hexavalent actinides equally well, no valence adjustment is necessary. The acid solution may be any strong mineral acid such as nitric, hydrochloric or perchloric acid. The acid concentration for the feed solution must be adjusted to between 0.1 and 10.0 M preferably 0.5 and 5.0 M for nitric acid and from 0.35 to 6 M, preferably between 0.5 and 5.0 M for perchloric and from 6–12 M for hydrochloric acid in order for the values to extract well. The feed solution may also be made from 0.05 to 0.3 M, preferably about 0.18–0.2 M, in oxalic acid. The oxalic acid complexes any iron, zirconium or molybdenum values which may be present in the waste solution to prevent them from being coextracted with the lanthanide and actinide values.

The extractant may be one of a series of several neutral bifunctional organophosphorous compounds containing a phenyl substituent. Generally, the compounds are alkyl(phenyl)-N,N-dialkylcarbamoylmethylphosphine oxides having the structural formula:

where R' is a straight or branched alkyl or alkoxyalkyl containing 6 to 12 carbon atoms and R'' is an alkyl containing 3 to 6 carbon atoms. The new group of extractants will hereinafter be collectively referred to as CMPO.

The addition of the phenyl group was found to unexpectedly increase the bonding strength of the compound for lanthanides and actinides at high acidities and lower the bonding strength of the compound for the same group of elements at low acidities relative to similar prior art compounds which contained two alkyls on the phosphorous atom. This, however, resulted in a compound with limited solubility in diluents and which readily formed a second organic phase upon even a small amount of loading. An increase in the length of the amide alkyls to at least 3 carbon atoms, preferably to the isobutyl alkyl, restored most of the solubility and eliminated the second phase formation in aromatic diluents. The alkyl or alkoxylalkyl substituent attached to the phosphinyl group is preferably straight chained, such as a n-octyl or it may be branched such as 2-ethylhexyl. Other satisfactory groups include 2,4,4-trimethylpentyl and 6-methylheptyl. The extractants are prepared and purified as described in *Separation Science and Technology*, 17(10) pp. 1261–1279, 1982, incorporated herein by reference.

The diluent may be any inert, water immiscible aromatic or aliphatic hydrocarbon such as diethylbenzene (DEB), diisopropylbenzene, xylene, decalin, dodecane, or kerosene or a chlorinated hydrocarbon such as carbon tetrachloride, or a hydrogen bonding diluent such as a water immiscible carboxylic acid. Diluent flash points should be above 80° C., so that the preferred diluent for fuel reprocessing is normal paraffin hydrocarbon containing a mixture of 10 to 14 carbon atoms, the longer carbon chains, i.e. $C_{12}$ and $C_{13}$ being more preferred because the lower volatility reduces fire and other hazards. However, extractant loading with the longer carbon chain diluents is substantially reduced and a second organic phase forms which makes extraction more difficult.

Generally phase modifiers are added to extraction solutions to improve the solubility of the extractant in the organic diluent and to reduce or eliminate the formation of the second organic phase, particularly when the extractant is loaded with metal ion. Phase modifiers may bond with the extractant and in so doing, compete with and reduce the extraction sites available for bonding with the metal ions, resulting in reduced extraction power. However, it has been found that by combining the CMPO extractant of the invention with a second organic compound, it is possible to reduce the concentration of the CMPO in the extraction solution while retaining or enhancing the extraction capability. Furthermore, it has been found that the addition of a phase modifier to the extraction solution substantially increases the loading of the extraction solution when used with normal paraffin hydrocarbon diluents.

The phase modifier may be a phosphate extractant such as tri-n-buty phosphate, (TBP), dibutyl butylphosphonate, (DBBP), or tris(2-ethylhexyl)phosphine oxide or it may be a nonphosphorus-based extractant which contains a basic donor group, e.g. sulfoxides, amides or ketones, such as dihexylsulfoxide (DHSO) and methylisobutyl ketone.

The amount of modifier in the extraction solution is dependent upon the acid concentration of the feed solution and, if a normal paraffin hydrocarbon diluent is used, upon the carbon chain length of the hydrocarbons. Higher acid concentrations and longer carbon chains in the diluent require more modifier to minimize third phase formation on loading the extraction solution. The amount of modifier is also dependent upon the amount of CMPO present in the extractant solution. The ratio of extractant to modifier may vary from about 1:5 to 1:8, while the amount of extractant present when used with a modifier such as TBP may vary from about 0.1 to 0.3, preferably 0.2 M. Thus, modifier concentration in the extraction solution may vary from about 0.5 to about 2.4 M, depending upon the ratio and extractant concentration.

By increasing the ratio of TBP to CMPO in the extraction solution, most of the CMPO extractant loading capacity can be regained. For example, an increase in the TBP ratio from about 1:6 to 1:7 might be necessary in a diluent having a higher percentage of $C_{14}$ hydrocarbon.

The acid content of the feed solution may vary from about 0.5 to about 6.0 molar and higher if hydrochloric acid feed solution were present. At the higher acid concentrations, extractant loadings are substantially reduced unless the ratio of TBP is increased. For example, with a nitric acid concentration of 6 M a TBP ratio of 1:7 might be necessary, while with a 6 M nitric acid together with a diluent having a high percentage of $C_{14}$ chains might together require a ratio of 1:8.

Thus, precise extractant concentrations and modifier ratios will depend upon feed solution, acid concentrations, and diluent composition and can be readily determined by one skilled in the art.

The loaded extraction solution, after contact with the feed solution, may be contacted with a 0.1 to 10.0 M, preferably 0.5 to 5.0 M nitric acid solution to scrub any fission product values which may have co-extracted with actinide and lanthanide values. The scrub solution may contain a small amount of oxalic acid, 0.01 to 0.05 M, preferably about 0.03 M to complex any fission product values to assist in their removal from the extractant.

If oxalic acid is used in the scrub solution, a second scrub solution consisting of 0.5 M $HNO_3$ and 0.01 M $Fe^{3+}$ as ferric nitrate is used to remove the small amounts of oxalic acid complexed in the organic phase. Removal of oxalic acid from the organic phase before stripping is necessary to avoid precipitating lanthanides and actinides.

The actinide and lanthanide values may be recovered by contacting the loaded extractant with an aqueous acid solution which is less than 0.05 M in acid to strip the extracted values from the extraction solution. Preferably the strip solution is from 0.01 to 0.02 M in nitric acid.

The extraction temperature is not critical and may be carried out over a range from about 25° to 75° C. with 40° C. generally preferred due to the self-heating effect of the radioactive solutions. In general, contact times are not critical, although 30 seconds has been found satisfactory to ensure phase mixing. The actual extraction operation can be carried out in batch or continuous operations, using, for example, simple mixer-settlers, direct or countercurrent flow, centrifigal contactors, liquid-liquid extraction in a chromatographic column or using similar conventional type equipment known to those skilled in the art. Phase ratios can be varied depending upon engineering considerations and economic factors.

The extractants of the invention are particularly unique in being able to modify the Purex process extractant in order to recover multivalent lanthanide and actinide values not otherwise readily recoverable from acidic waste solutions. The Purex process utilizes from about 5 to about 50, generally about 30 weight percent TBP in a normal paraffin hydrocarbon, such as tridecane, as an extractant for hexavalent uranium and tetravalent plutonium from about a 1.0 to 3.0 nitric acid feed solution. The Purex process will not extract trivalent actinides or lanthanides, and since the major radioactive component of many acidic radioactive waste solutions is trivalent amercium, the Purex extractant cannot be used on radioactive waste solutions unless extensive treatment of the waste solution is made first.

The Purex process extractant can be readily modified by the addition of, for example, about 5-10, preferably about 8 weight percent CMPO to make the extractant from about 0.1 to 0.3 M in CMPO and thereafter adjusting the TBP content to obtain a CMPO to TBP ratio of between about 1:5-8 as necessary depending upon acid content of the acidic waste solution and the hydrocarbon chain length of the diluent.

Figure 1:
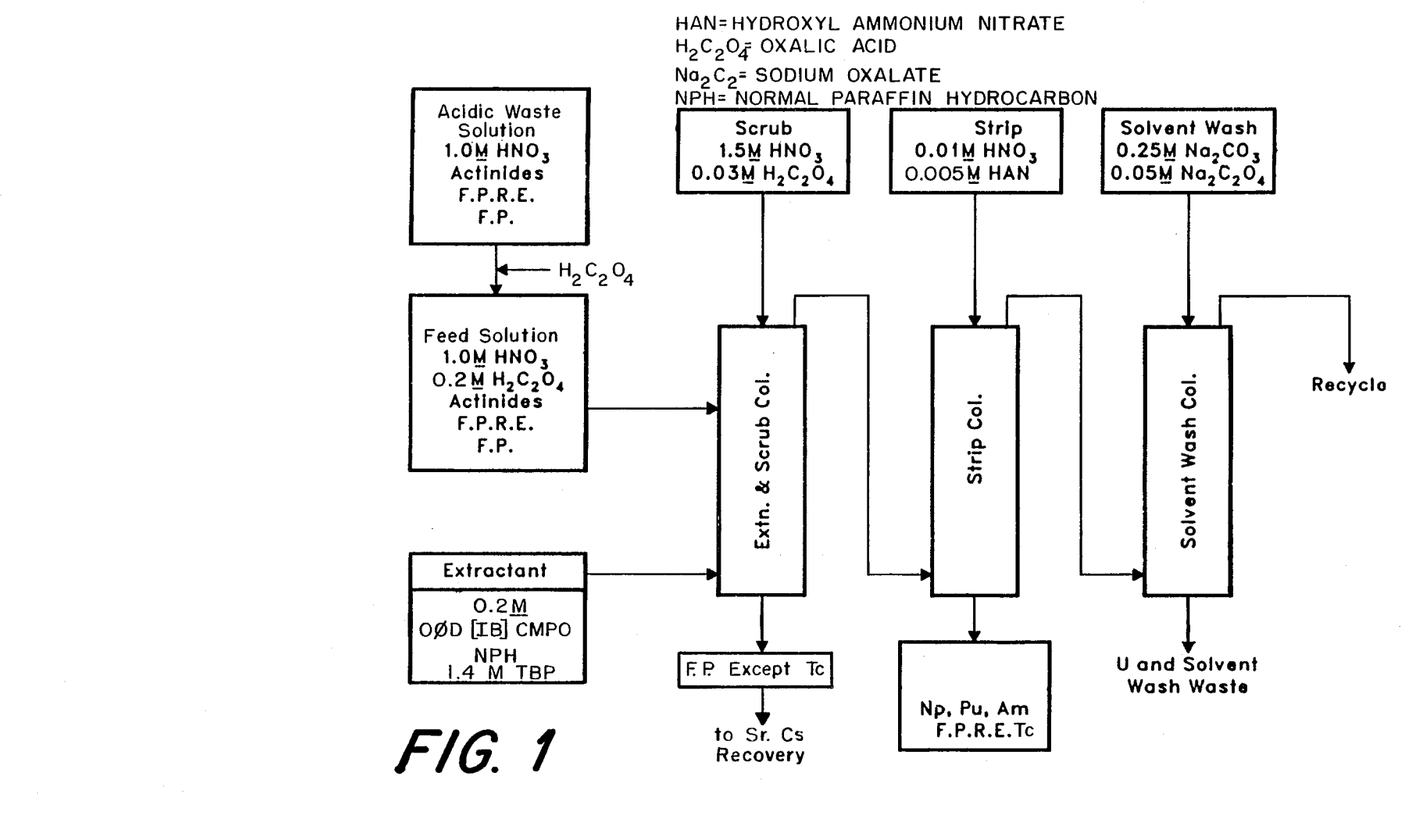
FIG. 1 is a flow sheet for the recovery of multivalent actinide and lanthanide values from a Purex acid waste solution.

A flow diagram for the recovery of actinide and lanthanide values from a Purex acid waste solution is shown in FIG. 1. The acid waste solution which may be about 1.0 M in nitric acid and containing fission products and rare earth fission products in addition to multivalent actinides is made about 0.2 M in oxalic acid to complex any iron, zirconium or molybdenum values which may be present, forming a feed solution.

The feed solution is then contacted with the organic extraction solution which is about 0.2 M O$\phi$D[IB]CMPO and 1.2 M TBP in a normal paraffin hydrocarbon which extracts the fission product rare earths and the multivalent actinide values away from the feed solution, leaving the iron, zirconium or molybdenum values with the feed. The relative flow rates between the feed and the extraction solution is about 1:0.4.

The loaded extraction solution is then contacted with about ½ volume of a 1.5 M HNO$_3$ solution scrub solution containing about 0.03 M oxalic acid to achieve additional decontamination from poorly extracted fission and corrosion products present in the feed.

The scrubbed extraction solution is then contacted with ½ volume of a stripping solution consisting of about 0.02 M HNO$_3$ and about 0.1 M hydroxylammonium nitrate (HAN) which removes the neptunium, plutonium, americium and fission product rare earth values. The HAN is necessary to replace the platinum to the trivalent state to prevent plutonium polymer formation. These values can then be concentrated for storage or further separated.

The stripped extraction solution is then washed with ¼ volume of a solvent wash of 0.25 M sodium carbonate and 0.05 M sodium oxalate to remove any degradation products from the extraction solution which can then be recycled.

Additional selectivity from certain values can also be obtained depending upon the choice of CMPO extractant. For example, in the flow chart as shown in FIG. 1, using O$\phi$D[IB]CMPO, technetium remains with and is recovered with the neptunium, plutonium and americium. However, substituting 2-EH$\phi$[IB]CMPO will send the technetium with the fission products.

The following Examples are given to illustrate the process of the invention and are not to be taken as limiting the scope of the invention as defined by the appended claims.

EXAMPLE I

Figure 2:
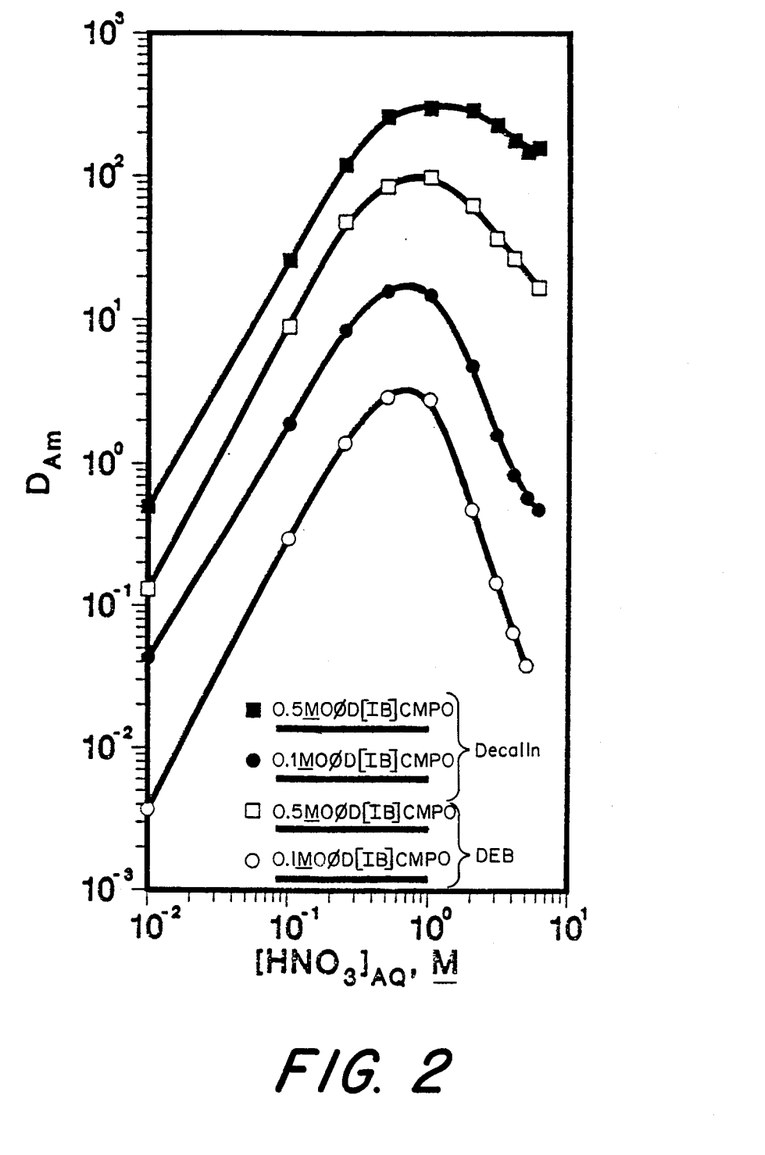
FIG. 2 is a graph showing the acid dependency of Am extraction for 0.1 M and 0.5 M O$\phi$D[IB]CMPO in decalin and DEB.

The acid dependency of americium was compared with O$\phi$D[IB]CMPO in decalin [decahydronaphthalene] and diethylebenzene [DEB] as diluents. Decalin was used because it was known that tracer Am loadings over a range of nitric acid concentrations in the absence of a phase modifier would not form a second organic phase. Extraction studies were made using various nitric acid concentrations and 0.5 and 0.1 M O$\phi$D[IB]CMPO in the two diluents. Standard radiometric assay and counting procedures were used throughout. Distribution ratios were determined at 25° C. The results are shown in FIG. 2. The Figure shows the increase in $D_{Am}$ when decalin is substituted for DEB. Also shown is the greater sensitivity of $D_{Am}$ to acidity at lower extractant concentrations in both DEB and decalin. However, $D_{Am}$ is less sensitive to acidity at both concentrations when decalin is the diluent.

EXAMPLE II

Figure 3:
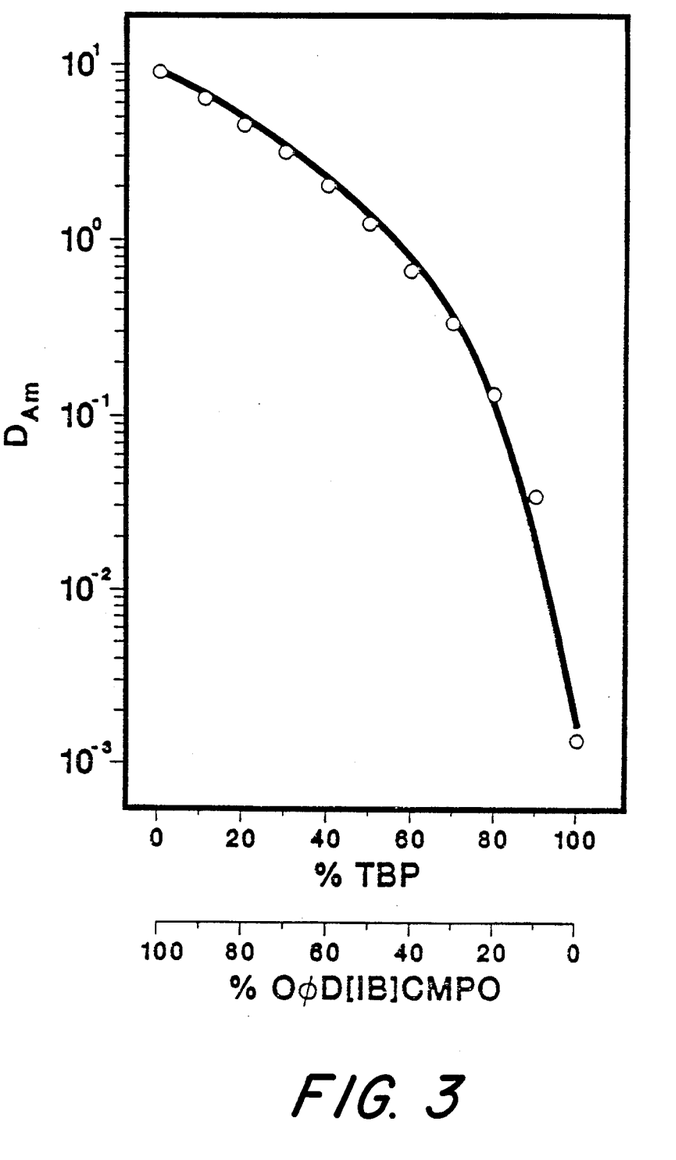
FIG. 3 is a graph showing the $D_{Am}$ for a 0.5 M extraction solution containing varying ratios of O$\phi$D[IB]CMPO and TBP in decalin from 6.0 M nitric acid feed solution.

An experiment was performed in which a combined O$\phi$D[IB]CMPO and TBP concentration of 0.5 M was continuously varied between 100% TBP and 100% O$\phi$D[IB]CMPO. A 6.0 M HNO$_3$ solution was used as the aqueous phase. The results are shown in FIG. 3. The circles represent experimental points while the solid line represents the calculated $D_{Am}$ based on the sum of the distribution ratios of the two extractants predicted for third power extractant dependency. The results indicate no mixed extractant species or synergistic effects are evident under these conditions.

EXAMPLE III

Figure 4:
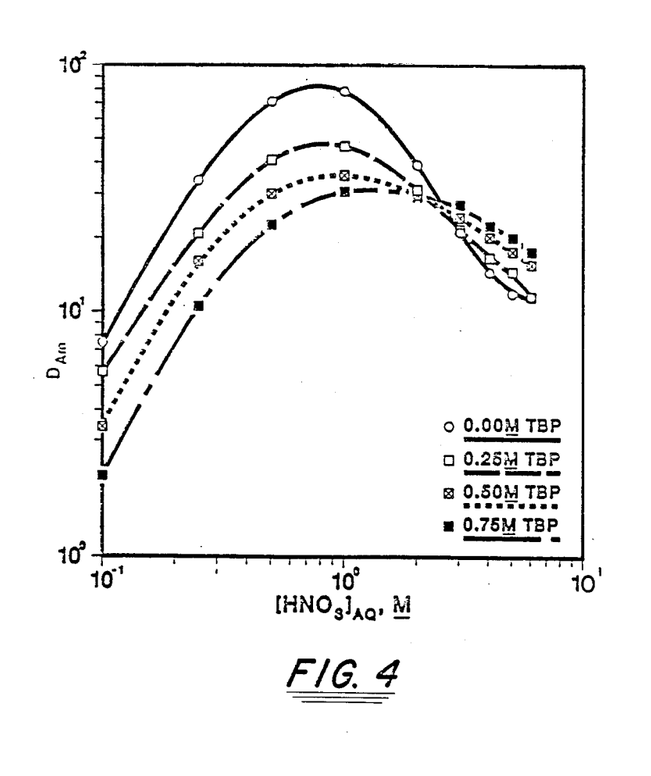
FIG. 4 is a graph showing the acid dependency of $D_{Am}$ for a 0.25 M solution of O$\phi$D[IB]CMPO in decalin containing several different concentrations of TBP.

In another experiment, increasing amounts of TBP were added to 0.25 M O$\phi$D[IB]CMPO in decalin. The results are shown in FIG. 4. A progressive increase in $D_{Am}$ as TBP increases is evident above 2 M HNO$_3$. The $D_{Am}$ at high acidities increased as much as a factor of 1.7 when the ratio of TBP to O$\phi$D[IB]CMPO was raised to three. It should be noted that the maximum $D_{Am}$ obtained with the highest concentration of TBP alone under these conditions is $<10^{-2}$. Thus, contributions to the overall distribution ratio by TBP can be ignored. This region of enhanced $D_{Am}$ with TBP addition may, by definition, be referred to as synergism, even though there is no evidence of mixed extractant TPB-CMPO/Am complex. Noted also is a decrease in $D_{Am}$ that ocurs at low acidities when the TBP concentration is increased to 0.75 M. This is important from the practical standpoint in that stripping of the loaded organic phase with water or dilute HNO$_3$ is facilitated due to the reduction of $D_{Am}$ at very low acidity.

EXAMPLE IV

Figure 5:
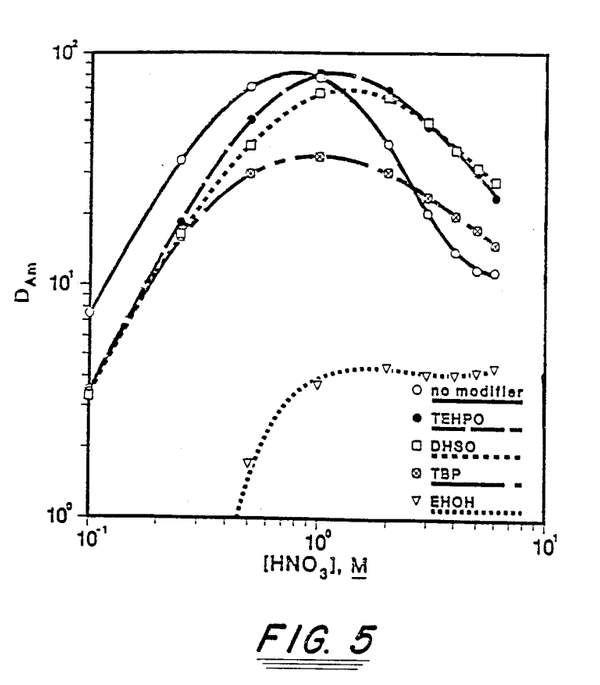
FIG. 5 is a graph showing the acid dependency for $D_{Am}$ extraction from HNO$_3$ by 0.25 M O$\phi$D[IB]CMPO in decalin with 0.5 M added of several different phase modifiers.

The acid dependency for Am(III) extraction from HNO$_3$ by 0.25 M O$\phi$D[IB]CMPO in decalin with several different modifiers was examined. The results are shown in FIG. 5. It is noted that the two most basic modifiers, TEHPO and DHSO, show much greater enhancement and slightly less suppression than TBP. Methylisobutyl ketone, although not shown, was found to follow the trend of TBP but to a lesser extent.

EXAMPLE V

Figure 6:
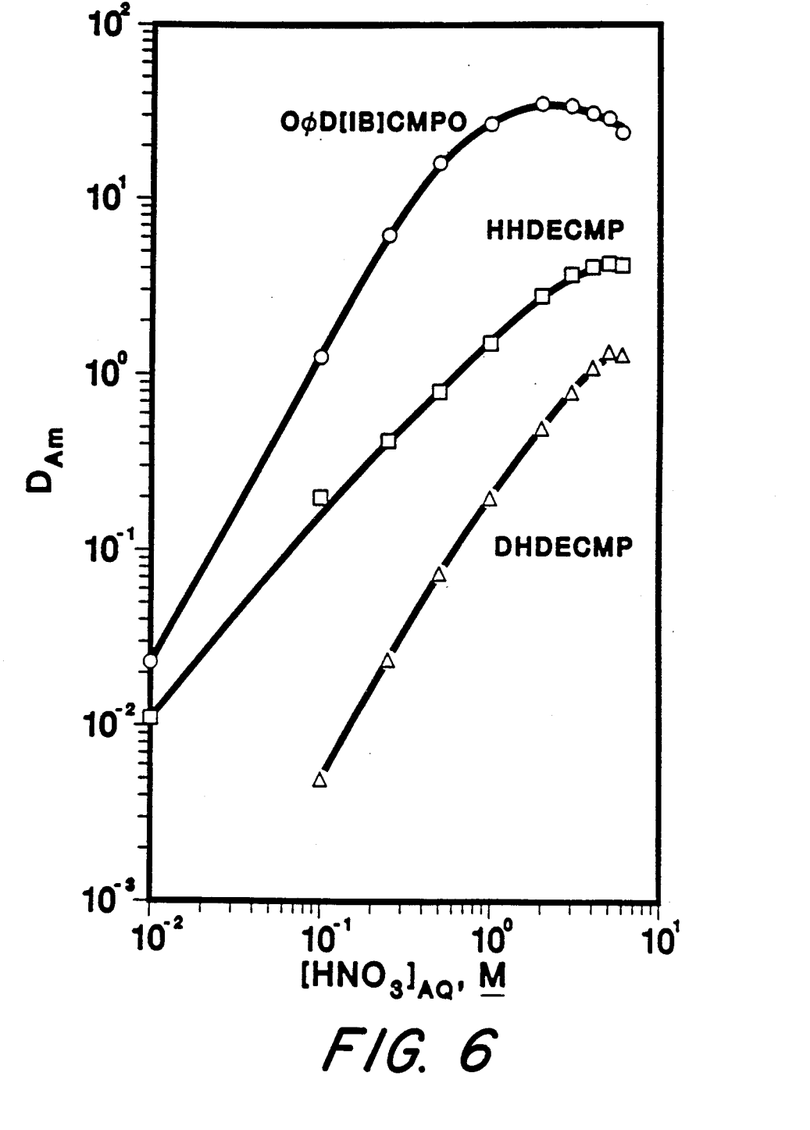
FIG. 6 is a graph showing the acid dependency of $D_{Am}$ by 0.2 M O$\phi$D[IB]CMPO and two prior art extractants in dodecane (a normal paraffin hydrocarbon) with TBP as a phase modifier.

A series of extractions were made with 0.2 M O$\phi$D-[IB]CMPO, HHDECMP and DHDECMP and 0.80 M TBP in n-dodecane to determine the acid dependency of americium. The results are shown in FIG. 6. No third phases were formed although solutions of these extractants alone in dodecane form a second organic phase in contact with nitric acid.

EXAMPLE VI

A series of extractions were made of Nd(III) in a 3 M HNO$_3$ solution with 1.2 M TBP in Norpar-12 TM [a normal paraffin hydrocarbon containing about 13% C$_{10}$, 36% C$_{11}$, 44% C$_{12}$ and 7% C$_{13}$], as a function of O$\phi$D-[IB]CMPO concentration. The results are given in Table I below:

| Conc of CMPO | Ratio TBP/CMPO | % Loading* |
|---|---|---|
| 0.20 | 6.0 | 70 |
| 0.25 | 4.8 | 55 |
| 0.30 | 4.0 | 45 |

*Percent loading is based on an extractant-to-metal ratio of 3

Although O$\phi$D[IB]CMPO cannot be loaded to saturation even with the highest TBP/extractant ratio without second organic phase formation, nevertheless loading is sufficiently high that the system 0.2 M O$\phi$D-[IB]CMPO, 1.2 M TBP-Norpar-12 TM can be used for the recovery of tri-, tetra-, and hexavalent actinides, and lanthanide fission products.

EXAMPLE VII

A series of extractions were made to determine the loading capacity of the extraction solution as a function of chain length of the diluent. Nd(III) as Nd (NO$_3$)$_3$ was extracted from a 3.0 M HNO$_3$ feed solution at 25° C. with 0.2 M O$\phi$D[IB]CMPO and 1.20 M TBP in different diluents. The extractant solution had been preconditioned by contact with a 3.0 M nitric acid solution. The results are given in Table 2 below.

TABLE 2

| Diluent | %, Loading $^{a,b}$ |
|---|---|
| Norpar-12 | 70–75 |
| Conoco$^d$ | 25–30 |
| Decane (C$_{10}$) | 100 |
| Dodecane (C$_{12}$) | 70–75 |
| Tridecane (C$_{13}$) | 30–35 |
| Tetradecane (C$_{14}$) | c |
| Hexadecane (C$_{16}$) | c |
| 100% C$_{12}$/0% C$_{13}$ | 70–75 |
| 75% C$_{12}$/25% C$_{13}$ | 50–55 |
| 50% C$_{12}$/50% C$_{13}$ | 45–50 |
| 25% C$_{12}$/75% C$_{13}$ | 30–35 |
| 0% C$_{12}$/100% C$_{13}$ | 30–35 |

$^a$Based on Nd/O$\phi$D[IB]CMPO mol ratio of 1:3.
$^b$The range of numbers means there was no third phase formation at the lower % but to higher % loading caused third phase formation.
$^c$Heavy organic forms with 3.0M NHO$_3$.
$^d$1% C$_{10}$, 2% C$_{11}$, 12% C$_{12}$, 56% C$_{13}$, 28% C$_{14}$, 1% C$_{15}$

EXAMPLE VIII

In a manner similar to Example VII, further extractions were made of Nd(III) from 1.0 M nitric acid solution. The results are given in Table 3 below.

TABLE 3

| Diluent | % Loading |
|---|---|
| Norpar-12 | ~100 |
| Conoco | 50–55 |
| C$_{10}$ | 100 |
| C$_{12}$ | ~100 |
| C$_{13}$ | 55–60 |
| C$_{14}$ | 30–35 |
| C$_{16}$ | <5 |

As is evident from the preceding discussion and examples, the combination of the CMPO extractants with a phase modifier provide a powerful extraction solution for the recovery of multivalent lanthanide and actinide values from acidic nuclear waste solutions. Most important is the ability to modify the Purex extractant by the addition of a small amount of CMPO to form an entirely new extraction solution capable of recovery of multivalent lanthanide and actinide values from nuclear reactor waste reprocessing solutions. The extraction solutions of the invention have been shown capable of reducing the TRU level to less than 100 n C/gm of solid wastes to be buried.

The embodiments of this invention in which an exclusive property or privilege is claimed are defined as follows:

1. A process for the recovery of multivalent lanthanide and actinide values from an aqueous acid solution containing these and other values comprising:
   adjusting the molarity of the acid in the aqueous solution to between 0.1 and 12.0 M to form a feed solution;
   contacting the feed solution with an extraction solution consisting of an organic extractant and a phase modifier in an inert water-immiscible organic diluent, the extractant having the formula:

where $\phi$ is phenyl, R' is a straight or branched alkyl containing from 6 to 12 carbon atoms and R'' is an alkyl containing from 3 to 6 carbon atoms, the phase modifier is selected from the group consisting of tri-n-butyl phosphate, dibutyl butylphosphonate, tris(2-ethylhexyl)phosphine oxide, dihexylsulfoxide and methylisobutyl ketone, whereby the multivalent lanthanide and actinide values are selectively extracted from the feed solution, thereby loading the extraction solution,
   separating the loaded extractant solution from the feed solution, and
   stripping the multivalent lanthanide and actinide values from the extraction solution.

2. The process of claim 1 wherein the extraction solution contains from about 0.1 to about 0.3 M in organic extractant, and the ratio between the extractant and the phase modifier is from about 1:5 to 1:8.

3. The process of claim 2 wherein the aqueous acid feed solution is a strong mineral acid selected from the group consisting of nitric, hydrochloric and perchloric acid.

4. The process of claim 3 wherein the aqueous feed solution is 0.1 to 10.0 M in nitric acid.

5. The process of claim 4 wherein the inert water-immiscible organic diluent is a normal paraffin hydrocarbon.

6. The process of claim 5 wherein the feed solution also contains from about 0.05 to 0.3 M oxalic acid.

7. The process of claim 6 wherein the feed solution is from about 0.5 to 5.0 M in nitric acid and about 0.2 M in oxalic acid.

8. The process of claim 7 wherein the lanthanide and actinide values are recovered by contacting the loaded extraction solution with an aqueous strip solution that is about 0.01 to 0.05 M in nitric acid.

9. The process of claim 8 wherein R' is selected from the group consisting of octyl, 2,4,4-trimethylpentyl, 6-methylheptyl and 2-ethylhexyl, and R'' is isobutyl.

10. The process of claim 9 including the additional step of contacting the loaded extraction solution with a 0.1 to 10.0 M nitric acid solution to scrub any fission product values from the solution which may have co-extracted with the lanthanide and actinide values.

11. The process of claim 10 wherein the scrub solution is from about 0.5 to 5.0 M in nitric acid and about 0.03 M in oxalic acid.

12. The process of claim 11 containing the additional step of contacting the scrubed extraction solution with a second scrub solution of about 0.5 M nitric acid and about 0.01 M ferric ion to remove oxalic acid remaining in the extraction solution.

13. The process of claim 12 wherein R' is octyl and the phase modifier is tri-n-butyl phosphate.

14. A process for the recovery of multivalent lanthanide and actinide values from an aqueous nitric acid nuclear fuel reprocessing waste solution containing multivalent lanthanide values, actinide values, fission product values and other metal values comprising:

adjusting the molarity of the acid solution to between 0.5 and 5.0 M and making the solution from about 0.05 to 0.3 M in oxalic acid to complex any iron, zirconium or molybdenum values which may be present, forming a feed solution, contacting the feed solution with an organic extraction solution consisting of an organic extractant and a phase modifier in an inert water-immiscible organic diluent, the extractant having the formula:

where $\phi$ is phenyl, R' is a straight or branched alkyl containing from 6 to 12 carbon atoms and $R^2$ is an alkyl containing from 3 to 6 carbon atoms, the phase modifier is selected from the group consisting of tri-n-butyl phosphate, dibutyl butylphosphonate, tris(2-ethylhexyl)phosphine oxide, dihexylsulfoxide and methylisobutyl Ketone, whereby the multivalent lanthanide and actinide values are selectively extracted from the feed solution, thereby loading the extraction solution, contacting the loaded extraction solution with an aqueous scrub solution which is from about 0.1 to 10.0 M nitric acid and about 0.01 to 0.05 M in oxalic acid to remove fission products which may have been co-extracted, contacting the scrubed extraction solution with a second scrub solution which is about 0.5 M $HNO_3$ and 0.01 M Fe, to remove extracted oxalic acid, contacting the scrubbed extraction solution with a stripping solution of from about 0.01 to 0.05 M in nitric acid and from about 0.005 to 0.02 M hydroxylammonium nitrate to recover the neptunium, plutonium, americium, and lanthanide fission product values from the loaded extractant, thereby recovering the multivalent lanthanide and actinide values from the acid waste solution.

15. The process of claim 14 including the additional step of contacting the stripped extraction solution with a wash solution consisting of about 0.1 to 0.5 M sodium carbonate and 0.01 to 0.1 sodium oxalate to remove degradation products from the extraction solution, and recycling the extraction solution.

16. The process of claim 15 wherein R' is selected from the group consisting of octyl, 2,4,4-trimethylpentyl, 6-methylheptyl and 2-ethylhexyl, and $R^2$ is isobutyl and the diluent is a normal paraffin hydrocarbon.

17. The process of claim 16 wherein the phase modifier is tri-n-butyl phosphate.

18. A method for modifying an extraction solution consisting of about 5 to about 50 weight percent tri-n-butylphosphate in a normal paraffin hydrocarbon diluent to form a second extraction solution to extract multivalent lanthanide and actinide values from 0.1 to 10.0 M acid feed solutions comprising:

adding an organic extractant to the extraction solution to make the solution from about 0.1 to 0.3 M in the organic extractant, the extractant having the formula:

where $\phi$ is phenyl, R' is a straight or branched alkyl containing 6 to 12 carbon atoms and R" is an alkyl containing 3 to 6 carbon atoms, and adjusting the mole ratio between the organic extractant and the tri-n-butylphosphate to between 1:5 and 1:8, thereby forming a second extraction solution which will extract multivalent lanthanide and actinide values.

19. The method of claim 18 wherein R' is selected from the group consisting of octyl, 2,4,4-trimethylpentyl, 6-methyl heptyl and 2-ethylhexyl, and R" is isobutyl.

20. The method of claim 19 wherein R' is octyl.

* * * * *